United States Patent [19]

Vrona et al.

[11] Patent Number: 5,490,504
[45] Date of Patent: Feb. 13, 1996

[54] ENDOTRACHEAL TUBE ATTACHMENT DEVICE

[75] Inventors: David W. Vrona; Michael R. Lavender, both of Vernon Hills; James J. Peterson, Island Lake; Margo E. Love, Round Lake Beach, all of Ill.

[73] Assignee: Hollister Inc., Libertyville, Ill.

[21] Appl. No.: 262,937

[22] Filed: Jun. 21, 1994

[51] Int. Cl.⁶ ................................................. A61M 25/01
[52] U.S. Cl. .............................. 128/207.17; 128/207.14; 128/911; 128/912; 128/DIG. 26
[58] Field of Search ...................... 128/204.18, 207.17, 128/911, 912, DIG. 26, 207.14

[56] References Cited

U.S. PATENT DOCUMENTS

| | | | |
|---|---|---|---|
| 2,590,006 | 3/1952 | Gordon | 128/206 |
| 2,831,487 | 4/1958 | Tafilaw | 128/350 |
| 3,017,887 | 1/1962 | Heyer | 128/DIG. 26 |
| 3,046,989 | 7/1962 | Hill | 128/348 |
| 3,161,199 | 12/1964 | Shaw-Sands | 128/348 |
| 3,288,136 | 11/1966 | Lund | 128/133 |
| 3,677,250 | 7/1972 | Thomas | 128/348 |
| 3,713,448 | 1/1973 | Arrott | 128/351 |
| 3,760,811 | 1/1973 | Andrew | 128/DIG. 26 |
| 3,774,616 | 11/1973 | White et al. | 128/200.26 |
| 3,946,742 | 3/1976 | Eross | 128/351 |
| 3,972,321 | 8/1976 | Proctor | 128/348 |
| 3,976,080 | 8/1976 | Bornhorst et al. | 604/179 |
| 3,977,407 | 8/1976 | Coleman et al. | 128/348 |
| 3,987,798 | 10/1976 | McGinnis | 128/351 |
| 3,993,081 | 11/1976 | Cussell | 128/351 |
| 4,120,304 | 11/1978 | Moor | 128/348 |
| 4,122,857 | 11/1978 | Haerr | 128/348 |
| 4,141,524 | 2/1979 | Corvese | 248/70 |
| 4,142,527 | 3/1979 | Garcia | 128/348 |
| 4,191,180 | 3/1980 | Colley et al. | 128/207.17 |
| 4,223,671 | 9/1980 | Muto | 128/200.26 |
| 4,249,529 | 2/1981 | Nestor et al. | 128/207.17 |
| 4,270,529 | 6/1981 | Muto | 128/200.26 |
| 4,282,871 | 8/1981 | Chodorow et al. | 128/207.18 |
| 4,326,515 | 4/1982 | Shaffer et al. | 128/207.17 |
| 4,329,984 | 5/1982 | Kervin | 128/207.14 |
| 4,331,143 | 5/1982 | Foster | 128/207.17 |
| 4,344,428 | 8/1982 | Sherman | 128/207.14 |
| 4,351,331 | 9/1982 | Gereg | 128/207.17 |
| 4,378,012 | 3/1983 | Brown | 128/207.17 |
| 4,381,611 | 5/1983 | Wishman | 604/312 |
| 4,392,857 | 7/1983 | Beran | 604/179 |
| 4,437,463 | 3/1984 | Ackerman | 128/207.17 |
| 4,449,527 | 5/1984 | Hinton | 128/207.17 |
| 4,480,639 | 11/1984 | Peterson et al. | 128/207.18 |

(List continued on next page.)

OTHER PUBLICATIONS

Respironics, Inc.; Enotracheal Tube Holder Instruction Sheet; 1–93.
Olympic Medical; Olympic Endo–Lok; Date unknown.
Catalog Page; Date unknown.
SecureEasy™ advertising brochure No. 246017 of Respironics Inc.™ dated Jan. 3, 1991 (1 page).

Primary Examiner—Edgar S. Burr
Assistant Examiner—William J. Deane, Jr.
Attorney, Agent, or Firm—Tilton, Fallon, Lungmus & Chestnut

[57] ABSTRACT

An endotracheal tube attachment device for positively securing an endotracheal tube to a patient and allowing selective lateral positioning and locking of the tube without removing the device or tube from the patient is disclosed. The device comprises an elongated strip of flexible material adapted to be adhesively attached to an upper lip region of a patient and a tube holder which is slideably mounted upon the strip. The tube holder has an arm extending in a direction perpendicular to and away from the strip and a securement strap is provided for positively securing the tube along the length of the arm. Positioning and locking mechanisms are provided for allowing selective lateral positioning of the tube holder along the length of the strip and positively locking the tube holder and tube in a selected position. The tube holder also allows for efficient and easy longitudinal adjustment of the endotracheal tube in the patient's trachea which is often required soon after initial placement of the tube.

10 Claims, 2 Drawing Sheets

U.S. PATENT DOCUMENTS

| | | | |
|---|---|---|---|
| 4,496,357 | 1/1985 | Osburn | 604/336 |
| 4,520,813 | 6/1985 | Young | 128/207.17 |
| 4,537,192 | 8/1985 | Foster | 128/207.17 |
| 4,548,200 | 10/1985 | Wapner | 128/207.17 |
| 4,571,245 | 2/1986 | Hubbard et al. | 604/179 |
| 4,592,351 | 6/1986 | Smith et al. | 128/207.17 |
| 4,598,705 | 7/1986 | Lichtenberger | 128/200.26 |
| 4,622,034 | 11/1986 | Shattuck | 604/179 |
| 4,660,555 | 4/1987 | Payton | 128/207.18 |
| 4,683,882 | 8/1987 | Laird | 128/207.17 |
| 4,702,736 | 10/1987 | Kalt et al. | 604/180 |
| 4,738,662 | 4/1988 | Kalt et al. | 604/180 |
| 4,739,757 | 4/1988 | Edwards | 128/207.18 |
| 4,744,358 | 5/1988 | McGinnis | 128/207.17 |
| 4,744,946 | 10/1988 | Ackerman et al. | 128/207.18 |
| 4,804,374 | 2/1989 | Laskody | 604/280 |
| 4,867,154 | 9/1989 | Potter et al. | 128/207.17 |
| 4,906,234 | 3/1990 | Voychehouski | 128/207.17 |
| 4,986,815 | 1/1991 | Schneider | 604/180 |
| 5,009,227 | 4/1991 | Nieuwstad | 128/207.17 |
| 5,038,778 | 8/1991 | Lott | 128/207.17 |
| 5,042,477 | 8/1991 | Lewis | 128/207.17 |
| 5,154,706 | 10/1992 | Cartmell et al. | 604/307 |
| 5,167,630 | 12/1992 | Paul | 604/179 |
| 5,295,480 | 3/1994 | Zemo | 128/207.17 |
| 5,308,339 | 5/1994 | Kalt et al. | 604/180 |
| 5,345,931 | 9/1994 | Battaglia | 128/207.17 |
| 5,352,216 | 10/1994 | Shiono et al. | 604/312 |
| 5,368,024 | 11/1994 | Jones | 128/207.14 |

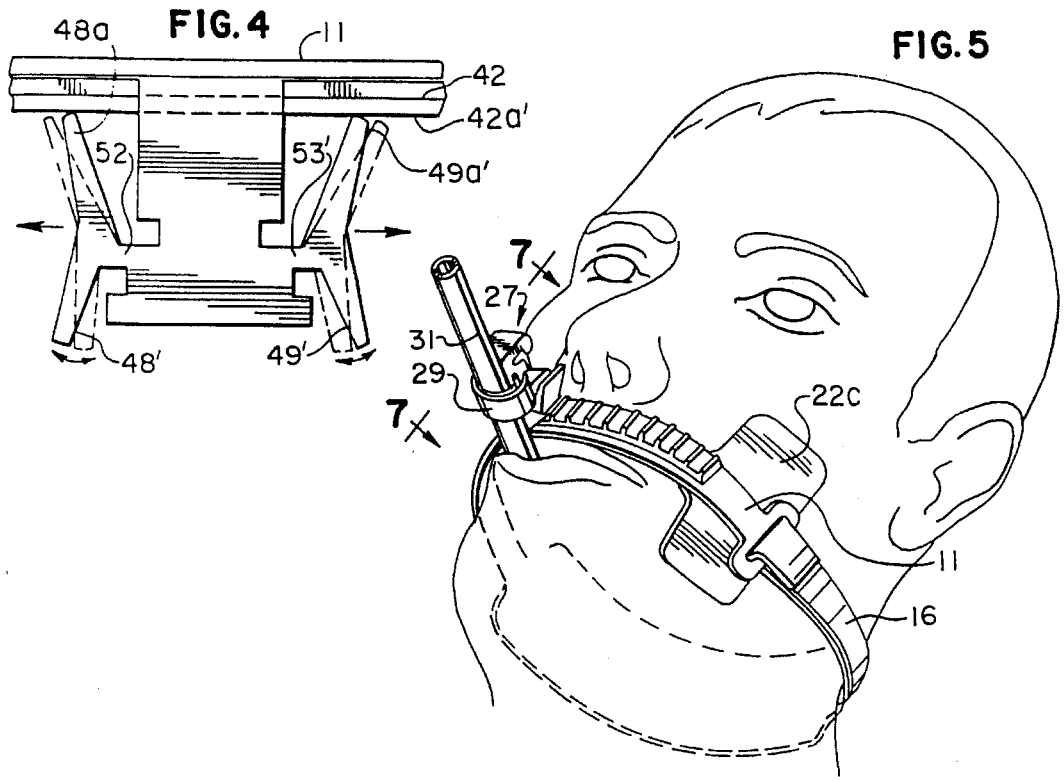
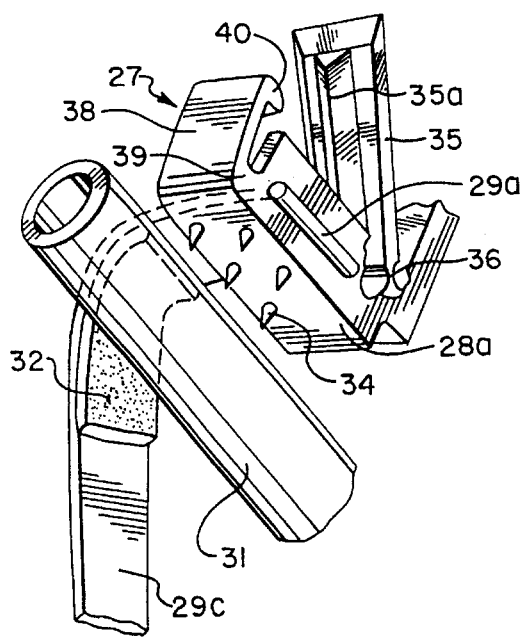
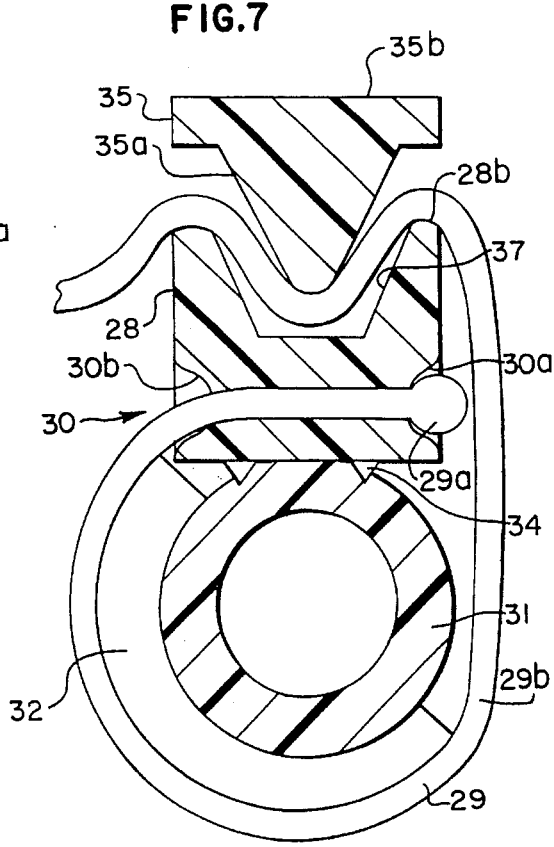

ENDOTRACHEAL TUBE ATTACHMENT DEVICE

BACKGROUND AND SUMMARY

Endotracheal tubes are commonly inserted through the mouth and into the trachea of patients to maintain an open airway and to allow mechanical assistance of breathing. Such tubes are often placed prior to surgery or are used on trauma or critically ill patients that may require intubation for extended periods of time. Many instances in which a patient is intubated require that the tube remain in place for approximately 48 to 72 hours and, in some circumstances, the period of use may be extended for 7 to 14 days. The most common method for securing an endotracheal tube on a patient is by using adhesive tape to adhere the tube to the patient's mouth and face. However, this method is not believed to be particularly effective as it does not provide positive positioning of the tube, it restricts access to the mouth, and the adhesive tape may add to the patient's discomfort of being intubated. Taping the tube in place also does not allow for easy repositioning of the tube, and maintaining the tube in one position, such as against one side of the mouth, is known to cause irritation and ulcering of the lips and surrounding skin. Consequently, nurses typically reposition the tube once every 24 hours which requires stripping away the adhesive tape from the patient's face and lips, repositioning the endotracheal tube, and then reapplying adhesive tape to secure the tube in place. While repositioning the tube at such intervals may prevent sores or ulcers from forming around the mouth, the repeated stripping away and re-attaching of adhesive tape to the mouth area itself often causes irritation and can be exceedingly uncomfortable for the patient. It is also a time-consuming operation that, if performed hastily or without sufficient care, could result in improper positioning of the tube at possibly serious risk to the patient's welfare.

Many devices are known for securing an endotracheal tube on a patient but it is believed that these devices are not particularly effective due to the continued and prevalent practice of using adhesive tape to position and secure endotracheal tubes. Such devices often take the form of face plates or complicated frames that attach to the patient's face and head and provide a means for securing the endotracheal tube in place. (See U.S. Pat. Nos. 4,537,192 and 4,867,154.) In addition to the complexity, a common shortcoming of such devices is that lateral repositioning of the tube is not easily achieved. One device that does allow lateral repositioning of the tube is disclosed by Muto in U.S. Pat. No. 4,270,529. The disclosed device includes a faceplate that fits over a patient's mouth and has an elongated slot with three positions. A tubular mouthpiece is positioned in the slot of the faceplate for inserting an endotracheal tube therethrough, and the mouthpiece and tube can be laterally adjusted into one of the three positions. A pair of opposed, flexible prongs are provided between each of the positions to provide resistance against the tube holder and prevent it from inadvertently switching positions during use. While this device allows for lateral repositioning of the tube without removing the device or tube from the patient, the faceplate member totally encircles the patient's mouth and restricts access thereto which is important for maintaining oral hygiene, taking of the person's temperature, and other similar oral procedures. Another shortcoming of such a device is that the opposed prongs between the three positions do not positively lock the tube in place and a patient (or attendant) may inadvertently cause the tube to change positions. It is also believed that when a nurse periodically shifts the position of the tube, the force applied to the tube to overcome the resistance of the prongs may be unpleasant for the patient and increase the overall discomfort often associated with being intubated.

An important aspect of this invention therefore lies in providing a device for positively fixing an endotracheal tube to a patient without unduly restricting access to the patient's mouth and allowing lateral repositioning and positive locking of the tube without removing the device or tube from the patient. Briefly, the endotracheal tube attachment device of this invention comprises an elongate strip of flexible material shaped to fit on a region adjacent to and along one lip, preferably the upper lip, of a patient, and band means for encircling the patient's head and connecting the ends of the strip. The inner surface of the strip is provided with adhesive pad means for securing the strip to the patient's face, and the pad means preferably takes the form of a skin barrier material having a layer of fluid-absorbing, hydrocolloid-containing adhesive having both wet and dry tack properties. A tube holder is slideably connected to the outer surface of the strip and has an arm extending in a direction perpendicular to the strip for attaching the endotracheal tube along a length of the arm. Securement means are provided for positively fixing the tube against the arm and the securement means may take the form of a soft, flexible strap having one end attached to the arm and a free length extending transversely from the arm for encircling the tube and securing it to the arm. Such a securement means allows for longitudinal adjustment of the tube by allowing the tube to be easily released and reattached to the tube holder after the tube is adjusted. Positioning means are provided for connecting the tube holder to the strip and allowing lateral sliding and repositioning of the holder along the strip, and locking means are provided for positively locking the holder and tube in a selected position. The locking means includes restraining means positioned on the strip and engaging means positioned on the tube holder for either engaging or disengaging the restraining means and respectively locking the tube holder in the selected position or allowing lateral sliding and repositioning of the tube holder along the strip.

In one embodiment, the positioning means takes the form of track means including an elongated rail of generally T-shaped configuration having a first member extending from an outer surface of the strip and a second cross-member parallel to the strip, and shuttle means including a retainer of generally C-shaped configuration disposed on the tube holder for receiving the cross-member of the rail and allowing lateral sliding of the retainer and tube holder along the length of the rail. In that embodiment, the engaging means of the locking mechanism may take the form of a pair of lever arms positioned on opposite sides of the shuttle means and extending in a direction generally perpendicular to the strip. The lever arms comprise distal end portions that engage the restraining means on the strip when the lever arms are in an unflexed condition, intermediate portions connected by flexible webs to the tube holder, and proximal end portions that when squeezed towards each other cause the lever arms to pivot about their intermediate portions which results in their distal end portions becoming disengaged from the restraining means. Where a T-shaped rail is used as the track means, the restraining means may comprise a smooth but resilient outer face of the cross-member of the rail that frictionally engages the distal end portions and prevents lateral movement of the tube holder. A longitudinal series of transversely-extending ratchet teeth may be disposed along the outer face of the rail to further prevent movement of the tube holder when the lever arms are in an unflexed condition.

In a preferred embodiment, the securement means for attaching the tube to the tube holder arm takes the form of a flexible strap having one end attached to the arm and a free length extending in a direction transverse to the arm, adhesive tape disposed on an inner surface of the strap, and clamping means for fixedly securing a segment of the strap along its free length to the arm when the strap is formed into a tube-retaining loop.

Other features, objects and advantages of the invention will become apparent from the specification and drawings.

DRAWINGS

FIG. 4 is a top plan view of another embodiment of the positioning and locking mechanisms of the present invention.

FIG. 5 is a perspective view of the endotracheal tube attachment device of this invention fixedly securing an endotracheal tube to a patient.

FIG. 6 is a perspective view of one embodiment of the securement means for attaching the endotracheal tube to the tube holder.

FIG. 7 is an enlarged cross-sectional view taken along line 7—7 of FIG. 5.

DETAILED DESCRIPTION OF PREFERRED EMBODIMENTS

Figure 1:
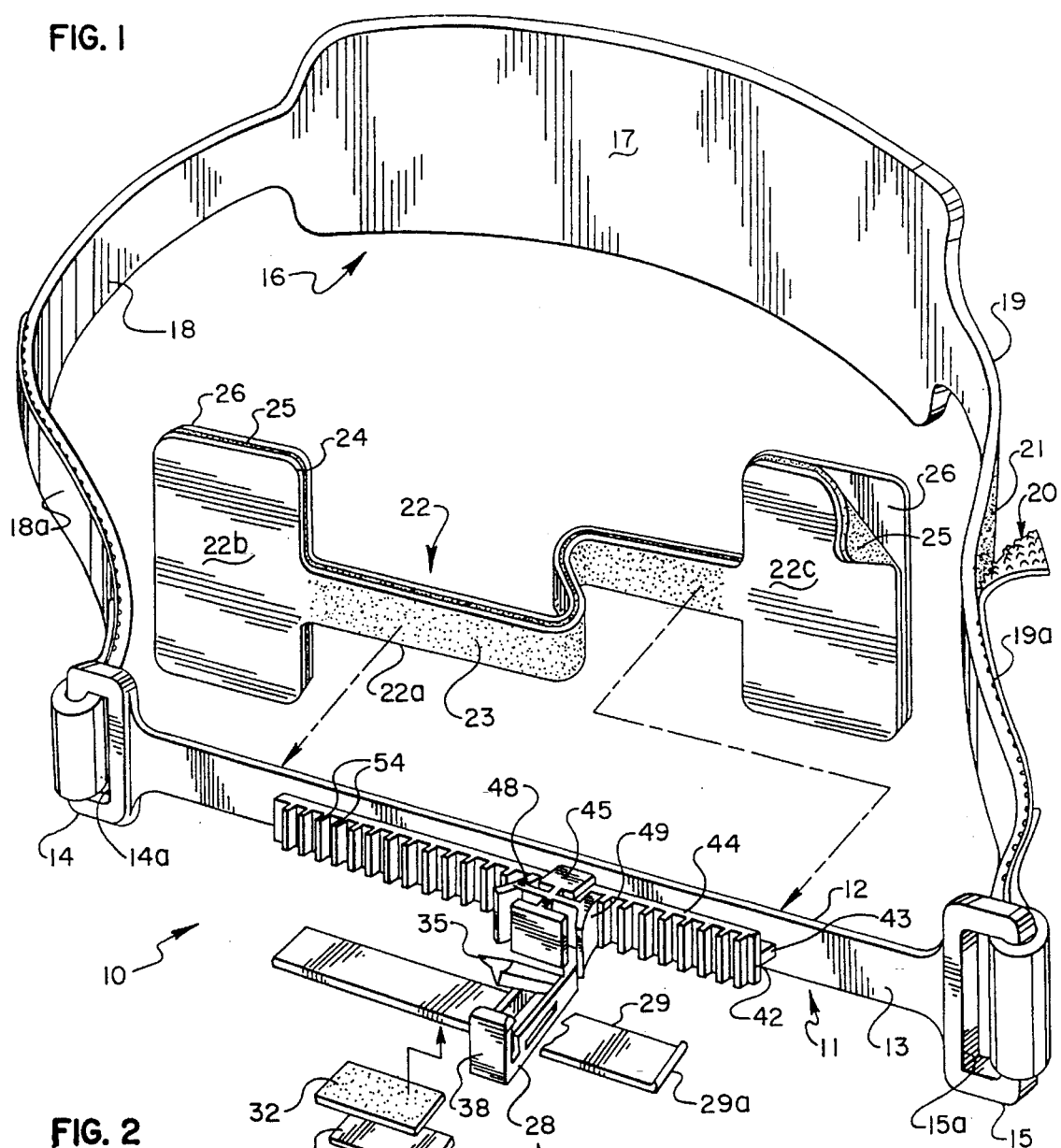
FIG. 1 is a perspective view of the endotracheal tube attachment device embodying this invention.

In FIG. 1, the numeral 10 generally designates an endotracheal tube attachment device having an elongated strip 11 of flexible material with inner and outer surfaces 12 and 13 and a pair of opposite ends 14 and 15. Strip 11 is preferably made of tough, flexible plastic material (e.g., polyethylene) and is shaped to fit on a region adjacent to and along one lip of the patient. Although strip 11 can be positioned along either of the patient's lips, it is believed preferable to position strip 11 along the patient's upper lip as illustrated in FIG. 5 due to the fact that if strip 11 were positioned along the lower lip, movement of the lower jaw might have adverse effects on the positioning of the endotracheal tube. Strip 11 is illustrated in FIG. 1 as having a linear and generally planar configuration in an unflexed or untensioned state and FIG. 5 illustrates strip 11 as being flexibly shaped to conform with the arcuate contour of a patient's upper lip. Although strip 11 is shown as being linear or planar when unflexed, it may, if desired, be preformed to have an arcuate configuration for easier positioning on the patient.

Ends 14 and 15 of strip 11 are provided with apertures 14a and 15a for attachment to head-encircling band means for securing the strip on the patient's head. Any type of band means may be employed to encircle the patient's head and connect ends 14 and 15, but the flexible, soft cloth band 16 shown in FIG. 1 has been found to be particularly effective for this purpose. Band 16 has an enlarged portion 17 that comfortably fits against the back of a patient's head and holds the band in place. Elongated strap portions 18 and 19 extend from enlarged portion 17 and can be threaded through respective apertures 14a and 15a, then reversed and attached to themselves by clamps (not shown) or, preferably, by using fabric loop and hook-type retainers commonly known and sold under the trademark "Velcro". Where Velcro is employed, flexible plastic end straps 18a and 19a with plastic (nylon) hooks 20 can be attached to the ends of strap portions 18 and 19 for attaching to the soft loop cloth 21 of straps 18 and 19.

Inner (bodyside) surface 12 of strip 11 is provided with adhesive pad means for comfortably attaching strip 11 along the patient's lip. The pad means preferably takes the form of pad 22 having a narrow elongated portion 22a and a pair of opposite, enlarged end portions 22b and 22c. Narrow elongated portion 22a is secured by a thin layer of adhesive 23, such as a liquid cyanoacrylate adhesive, to inner surface 12 of strip 11 and enlarged portions 22b and 22c are positioned adjacent ends 14 and 15 so that the junction of the head band and strap ends will not cause discomfort to the patient. In a preferred construction, pad 22 is composed of a first layer 24 of a resilient, flexible, fine-celled thermoplastic foam, such as polyolefin or polyurethane foam, and a second layer 25 of soft, deformable skin barrier material having both wet and dry tack properties. It is believed that skin barrier materials that employ fluid-absorbing, hydrocolloid-containing adhesives with both wet and dry tack are preferable, and particularly effective skin barrier materials are disclosed in co-owned U.S. Pat. No. 4,496,357. However, if desired, layer 24 may be formed of materials other than foam, such as a film of flexible polyurethane or other polymeric film having similar properties, and layer 25 may instead be formed of a suitable pressure-sensitive adhesive (e.g., a medical grade acrylic adhesive). Regardless of the particular composition of adhesive layer 25, a removable silicone-coated release sheet 26 is provided to cover the adhesive prior to use.

A tube holder, generally designated at 27, is slideably mounted upon strip 11 and has an arm 28 that extends in a direction perpendicular to strip 11 away from the outer surface 13 of that strip. Securement means are provided on arm 28 for securing an endotracheal tube thereto in a parallel direction. In a preferred form, the securement means comprises a soft, elongated strap 29 of elastomeric material, preferably a copolymer of etheylene and vinyl acetate, and an enlarged retaining portion 29a is formed on one end of the strap. As most clearly seen in FIG. 7, arm 28 is provided with a slot 30 for receiving strap 29, and slot 30 has a pair of recessed ends 30a and 30b for receiving retaining portion 29a and securely fixing that end of the strap to the arm. A free length 29b of strap 29 then extends in the direction transverse to arm 28 and may be formed into a tube-retaining loop for encircling and securing an endotracheal tube 31 along arm 28. An adhesive pad 32 formed of a suitable pressure-sensitive adhesive is provided on an inner surface 29c of strap 29 to further restrain tube 31 from rotational or longitudinal movement when it is secured against arm 28 by strap 29 (FIG. 6), and a removable silicone coated release layer 33 may be provided on pad 32 prior to use (FIG. 1). A plurality of sharp, nub-like prongs 34 may also be provided on a bottom 28a of arm 28 for frictionally engaging tube 31 and further restraining the tube from movement.

Clamping means are provided on arm 28 for securely engaging a segment of strap 29 along its free length 29b and maintaining the strap in tension to restrain a tube encircled by it. Such clamping means may take the form of an elongated, cantilevered clamping member 35 that is hingedly attached at 36 to tube holder 27 as most clearly seen in FIG. 6. Clamping member 35 can be pivoted and raised about hinged portion 36 to allow free length 29b of strap 29 to be folded over the top 28b of arm 28, and then clamping member 35 can be lowered and locked in place against arm 28 to maintain strap 29 in tension about tube 31. To crimp strap 29 and ensure that it does not slip out from between arm 28 and clamping member 35, clamping member 35 is preferably provided with a longitudinal rib 35a and arm 28 is provided with a longitudinal channel 37 for receiving rib 35a.

Latching means are provided to lock clamping member 35 against arm 28 with strap 29 interposed therebetween, and such latching means may take the form of a flexible, resilient latching member 38 that is flexible about its attachment point 39 to arm 28. A clip or hook portion 40 is provided on member 38 so that when clamping member 35 is lowered, latching member 38 will be pushed outwardly and pivot about attachment point 39 to allow clamping member 35 to tightly engage strap 29. Clip portion 40 then securely engages top 35b of clamping member 35 and locks clamping member 35 in place. When it is desired to release tube 31, a person may simply pull clip portion 40 of latching member 38 away from the tube holder until clip 40 is retracted beyond the end of clamping member 35, and clamping member 35 can then be raised to release strap 29. Such a construction allows for easy longitudinal adjustment of the endotracheal tube by releasing strap 29, and then resecuring the tube, after such adjustment, to the holder with strap 29. The ability to easily adjust the tube in the longitudinal direction is greatly advantageous as endotracheal tubes are often adjusted in the longitudinal direction shortly after initial placement if chest x-rays reveal that the tube is not in its optimal position.

Figure 2:
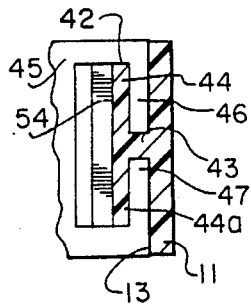
FIG. 2 is an enlarged cross-sectional view of one embodiment of the positioning means of the present invention.

Positioning means are provided for connecting tube holder 27 to strip 11 and allowing selective lateral positioning of the tube holder and tube along strip 11. Such positioning means preferably takes the form of track means disposed on outer surface 13 of strip 11 and shuttle means disposed on tube holder 27 for engaging the track means and allowing lateral sliding of the shuttle and tube holder along the track means. In one embodiment, the track means takes the form of rail 42 of a generally T-shaped cross-sectional configuration and including a first member 43 extending perpendicularly from outer surface 13 and a second cross-member 44 parallel to strip 11, as most clearly shown in FIGS. 1 and 2. The shuttle means may then take the form of retainer 45 having a generally C-shaped configuration. Retainer 45 has a pair of opposing arms 46 and 47 that fit relatively tightly between outer surface 13 of strip 11 and an inner face 44a of cross-member 44 to stabilize retainer 45 on rail 42 but without impeding lateral movement of retainer 45 along the longitudinal length of rail 42. Although retainer 45 and rail 42 have been described in considerable detail, it will be understood that different types of shuttle and track means may be employed as long as the shuttle means allows lateral sliding of tube holder 27 along strip 11 and enables the tube to be repositioned from one side of a person's mouth to the other. It will also be understood that stop members (not shown) may be provided on the ends of rail 42 to prevent retainer 45 from sliding off the track.

Figure 3:
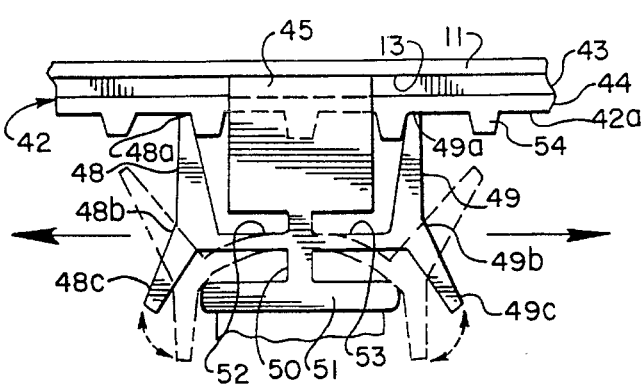
FIG. 3 is a top plan view of one embodiment of the positioning and locking mechanisms of the present invention.

The positioning means allows lateral positioning of tube holder 27 and tube 31 into any of a multiplicity of selected positions along strip 11, and locking means are provided for positively locking the tube holder and tube in the selected position of adjustment. The locking means includes restraining means disposed on strip 11 and engaging means disposed on tube holder 27 operable to selectively and positively engage or disengage the restraining means and respectively lock the tube holder in the selected position or allow lateral sliding of the tube holder along strip 11. A preferred form of engaging means is most clearly shown in FIG. 3 and comprises a pair of lever arms 48 and 49 that are positioned generally perpendicular to strip 11. Tube holder 27 includes a central member 50 and an end member 51 for mounting of the lever arms. Lever arms 48 and 49 include distal end portions 48a and 49a that are positioned to engage the restraining means on strip 11 when the arms are in an unflexed condition, intermediate portions 48b and 49b that are respectively connected by flexible webs 52 and 53 to central member 50, and proximal end portions 48c and 49c that when squeezed towards each other in a flexed condition cause the lever arms to pivot about their intermediate portions which results in distal end portions 48a and 49a becoming disengaged from the restraining means on strip 11 (shown by broken lines in FIG. 3). End member 51 is provided to contact proximal end portions 48c and 49c when the lever arms are flexed and serves as a stop to limit their pivotal movement so that a user only needs to apply as much force as necessary to disengage distal end portions 48a and 49b from the restraining means. In a preferred form, the restraining means comprises a longitudinal series of transversely-extending ratchet teeth 54 disposed along outer face 42a of rail 42.

In another embodiment of the restraining means (FIG. 4), the ratchet teeth may be eliminated and the lever arms can engage outer face 42a' of rail 42' which is smooth, but resilient, and adapted to frictionally engage distal end portions 48a' and 49a' by means of a wedging action, and lock tube holder 27 in a selected position of an infinite number of such positions when the lever arms are in unflexed condition. In such a construction, lever arms 48' and 49' preferably have a relatively rigid mounting so that distal ends 48a' and 49a' provide a tight wedging action against the outer surface of the rail. In the illustration given in FIG. 4, such a rigid mounting is provided by attaching lever arms 48' and 49' to tube holder 27 with short semi-flexible webs 52' and 53' which allow the lever arms to be flexed a sufficient distance to disengage their distal ends from track 42 while still providing sufficient stiffness to positively lock the tube holder in place when the lever arms are unflexed.

The endotracheal tube attachment device 10 of this invention is applied with the endotracheal tube 31 already positioned in the patient's mouth and trachea. Preferably, a bite block device is already prepositioned about the tube to prevent the patient from clamping the tube between his or her teeth. Such a bite block device is well known and compatible with the attachment device of this invention. The person applying the device then removes release layer 26 from adhesive pad 22 and applies and positions strip 11 adjacent to and along the lip, preferably the patient's upper lip. Band 16 is secured about the patient's head to secure strip 11 in place. The applier actuates lever arms 48 and 49 to allow lateral sliding of tube holder 27 into position so that arm 28 is positioned adjacent and parallel to tube 31, at which point lever arms 48 and 49 are released to positively lock tube holder 27 in position. Release layer 33 is then removed from adhesive 32 and the free length 29b of strap 29 is formed into a tube-retaining loop about tube 31. A segment of strap 29 is locked between clamping member 35 and channel 37 by lowering clamping member 35 below clip 40 which engages the top of clamping member 35 and securely locks strap 29 about tube 31. Once so positioned, strap 29, adhesive 32, and prongs 34 all act to prevent rotational and longitudinal movement of tube 31. Tube holder 27 and tube 31 can then be laterally repositioned as desired by actuating lever arms 48 and 49 to allow lateral sliding of the tube holder along the length of strip 11. One of the primary advantages of such a construction is that the tube can easily be repositioned and positively locked without requiring release of tube 31 from the tube holder 27. This is advantageous because if it were required to release tube 31, tube 31 might possibly shift longitudinally in the patient's trachea, requiring repositioning of the tube and possibly x-ray verification of the tube's placement which is time-consuming, expensive and potentially harmful.

While in the foregoing, embodiments of the invention have been disclosed in considerable detail for purposes of illustration, it will be understood by those skilled in the art that many of these details may be varied without departing from the spirit and scope of the invention.

We claim:

1. A device for securing an endotracheal tube to a patient and allowing selective lateral positioning and positive locking of the tube without removing the device or tube from the patient, said device comprising:

an elonqated strip of flexible material shaped to fit on a region adjacent to and along one lip of a patient, said strip having inner and outer surfaces and a pair of opposite ends;

adhesive pad means disposed on the inner surface of said strip for adhesively attaching the strip to said region of the patient;

a tube holder slidably connected to said strip and having an arm extending in a direction generally perpendicular to said strip, said tube holder including securement means for releasably attaching a tube along said arm;

positioning means for attaching said tube holder to said strip and allowing lateral sliding of said holder along a length of said strip; and locking means for positively locking said holder in a selected position along the length of said strip, said locking means including restraining means disposed on said strip and engaging means disposed on said tube holder for selectively engaging or disenlarging said restraining means and respectively locking said tube holder in a selected position or allowing lateral sliding of said tube holder along said strip;

said positioning means comprising track means disposed along said outer surface of said strip for enabling said tube holder to be slidably mounted thereon, and shuttle means disposed on said tube holder for engaging said track means and allowing lateral sliding of said tube holder along said track means;

said track means comprising an elongated rail of generally T-shaped configuration having a first member extending from said outer surface of said strip and a second cross-member parallel to said strip, and said shuttle means comprising a retainer of generally C-shaped configuration disposed on said holder and adapted to receive said cross-member of said rail such that said retainer and said tube holder are laterally slidable along said rail.

2. The device of claim 1 in which band means are provided for encircling a patient's head and connecting said ends of said strip to secure said strip on the patient.

3. The device of claim 1 in which said engaging means comprises a pair of lever arms positioned generally perpendicular to said strip and having distal end portions that engage said restraining means when said lever arms are in an unflexed condition, intermediate portions connected by flexible webs to said tube holder, and proximal end portions that when squeezed towards each other, cause said lever arms to pivot about said intermediate portions, thereby disengaging said distal end portions from said restraining means.

4. The device of claim 3 in which each of said lever arms are positioned on opposite sides of said shuttle means.

5. The device of claim 4 in which said restraining means comprises a smooth but resilient outer face of said track means positioned to frictionally engage said distal end portions of said lever arms when said lever arms are in said unflexed condition.

6. The device of claim 4 in which said restraining means comprises a longitudinal series of transversely-extending ratchet teeth disposed along said track means.

7. A device for securing an endotracheal tube to a patient and allowing selective lateral positioning and positive locking of the tube without removing the device or tube from the patient, said device comprising:

an elongated strip of flexible material shaped to fit on a region adjacent to and along one lip of a patient, said strip having inner and outer surfaces and a pair of opposite ends;

adhesive pad means disposed on the inner surface of said strip for adhesively attaching the strip to said region of the patient;

a tube holder slidably connected to said strip and having an arm extending in a direction generally perpendicular to said strip, said tube holder including securement means for releasably attaching a tube along said arm;

positioning means for attaching said tube holder to said strip and allowing lateral sliding of said holder along a length of said strip; and locking means for positively locking said holder in a selected position along the length of said strip, said locking means including restraining means disposed on said strip and engaging means disposed on said tube holder for selectively engaging or disengaging said restraining means and respectively locking said tube holder in a selected position or allowing lateral sliding of said tube holder along said strip;

said securement means comprising an elongated, flexible strap with one end attached to said arm of said tube holder and a free length extending in a direction transverse to said arm, adhesive means digposed on an inner surface of said free length for securing a tube thereto, and clampAng means positioned on said arm for fixedly securing a segment of said strap along its free length to said arm when said strap is formed into a tube-retaining loop;

said clamping means comprising a clamping member hingedly attached to said tube holder, a receiving channel disposed along the length of said arm, and a releasable latching means for locking said clamping member along said receiving channel when a segment of said strap is inserted between said clamping member and said channel.

8. The device of claim 7 in which said adhesive pad means includes a layer of fluid-absorbing, hydrocolloid-containing adhesive material having both wet and dry tack properties.

9. A device for securing an endotracheal tube to a patient and allowing selective lateral positioning and positive locking of the tube without removing the device or tube from the patient, said device comprising:

an elongated strip of flexible material shaped to fit on a region adjacent to and along one lip of a patient, said strip having inner and outer surfaces and a pair of opposite ends;

a tube holder slidably connected to said strip and having an arm extending in a direction perpendicular to said strip, said tube holder including securement means for releasably attaching a tube along said arm; and locking means for positively locking said holder in a selected position along the length of said strip, said locking means comprising a pair of lever arms disposed on said tube holder and positioned generally perpendicular to said strip, said lever arms being pivotally mounted on said tube holder and having distal end portions that engage said strip and lock said tube holder in a selected position when said lever arms are in a unflexed condition and that disengage from said strip and allow lateral sliding of said tube holder when said lever arms are in a flexed condition.

10. An endotracheal tube securement device comprising:

an elongated strip of flexible material shaped to fit on a region adjacent to and along one lip of a patient, said strip having inner and outer surfaces and a pair of opposite ends;

a tube holder slidably connected to said strip and having an arm extending in a direction perpendicular to said strip;

positioning means for attaching said tube holder to said strip and allowing lateral sliding of said holder along the length of said strip; and securement means disposed on said arm of said tube holder for releasably attaching a tube along said arm, said securement means including an elongated, flexible strap with one end attached to said arm of said tube holder and a free length extending in a direction transverse to said arm, a clamping member hingedly attached to said tube holder, and releasable latching means for locking said clamping member along said arm to secure said strap around a tube when a segment of said strap is inserted between said clamping member and said arm.

* * * * *